(12) United States Patent
Hoenes et al.

(10) Patent No.: US 8,152,741 B2
(45) Date of Patent: Apr. 10, 2012

(54) LANCET WHEEL

(75) Inventors: Joachim Hoenes, Zwingenberg (DE); Hans List, Hesseneck-Kailbach (DE); Volker Zimmer, Laumersheim (DE); Christian Hoerauf, Oftersheim (DE); Uwe Kraemer, Ilvesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 195 days.

(21) Appl. No.: 12/235,891

(22) Filed: Sep. 23, 2008

(65) Prior Publication Data

US 2009/0099477 A1  Apr. 16, 2009

(30) Foreign Application Priority Data

Oct. 15, 2007  (EP) .................................. 07020148

(51) Int. Cl.
*A61B 5/00* (2006.01)
*A61B 17/14* (2006.01)
*A61B 17/32* (2006.01)

(52) U.S. Cl. ........................................ 600/583; 606/181

(58) Field of Classification Search .................. 600/583, 600/584, 573; 606/181–183
See application file for complete search history.

(56) References Cited

U.S. PATENT DOCUMENTS

| 4,794,926 | A | 1/1989 | Munsch et al. |
| 5,829,589 | A | 11/1998 | Nguyen et al. |
| 6,228,100 | B1 | 5/2001 | Schraga |
| 7,004,928 | B2 | 2/2006 | Aceti et al. |
| 7,150,755 | B2 | 12/2006 | Levaughn et al. |
| 7,192,405 | B2 | 3/2007 | DeNuzzio et al. |
| 7,223,248 | B2 | 5/2007 | Erickson et al. |
| 7,343,188 | B2 | 3/2008 | Sohrab |
| 2002/0052618 | A1 | 5/2002 | Haar et al. |
| 2002/0120216 | A1 | 8/2002 | Fritz et al. |
| 2002/0130042 | A1 | 9/2002 | Moerman et al. |
| 2003/0211619 | A1 | 11/2003 | Olson et al. |
| 2003/0212347 | A1 | 11/2003 | Sohrab |
| 2004/0039303 | A1 | 2/2004 | Wurster et al. |
| 2004/0064068 | A1 | 4/2004 | DeNuzzio et al. |
| 2004/0102803 | A1 | 5/2004 | Boecker et al. |
| 2004/0193202 | A1 | 9/2004 | Allen |
| 2005/0036909 | A1 | 2/2005 | Erickson et al. |
| 2005/0277850 | A1 | 12/2005 | Mace et al. |
| 2006/0064035 | A1 | 3/2006 | Wang et al. |
| 2006/0094985 | A1 | 5/2006 | Aceti et al. |
| 2006/0200044 | A1 | 9/2006 | Freeman et al. |
| 2006/0204399 | A1 | 9/2006 | Freeman et al. |
| 2007/0142748 | A1 | 6/2007 | Deshmukh et al. |
| 2007/0173741 | A1 | 7/2007 | Deshmukh et al. |
| 2007/0179406 | A1 | 8/2007 | DeNuzzio et al. |

(Continued)

FOREIGN PATENT DOCUMENTS

CN  1456887 A  11/2003

(Continued)

*Primary Examiner* — Brian Szmal
(74) *Attorney, Agent, or Firm* — Woodard, Emhardt, Moriarty, McNett & Henry LLP

(57) ABSTRACT

The invention is related to a lancet wheel (1) having a plurality of lancets (2) in a ring-shaped arrangement, the lancets (2) comprising a lancet body (4) that ends in a lancet tip (3). A lancet wheel (1) according to the invention has a carrier (5) that carries the lancets (2), whereby the lancets (2) are connected to the carrier (5) via bars (7, 7a, 7b, 7c) that allow for mobility of the lancets (2) relative to the carrier (5).

18 Claims, 2 Drawing Sheets

U.S. PATENT DOCUMENTS

| | | |
|---|---|---|
| 2008/0009768 A1 | 1/2008 | Sohrab |
| 2008/0021346 A1* | 1/2008 | Haar et al. .................... 600/583 |
| 2008/0269791 A1* | 10/2008 | Hoenes et al. ................ 606/181 |
| 2010/0174211 A1* | 7/2010 | Frey et al. .................... 600/583 |

FOREIGN PATENT DOCUMENTS

| | | |
|---|---|---|
| EP | 1 203 563 A2 | 5/2002 |
| EP | 1 360 934 A1 | 11/2003 |
| EP | 1 360 935 A1 | 11/2003 |
| EP | 1 402 812 A1 | 3/2004 |
| EP | 1 508 304 A1 | 2/2005 |
| WO | WO 2003/070099 A1 | 8/2003 |
| WO | WO 2005/006939 A2 | 1/2005 |
| WO | WO 2005/016125 A2 | 2/2005 |
| WO | WO 2005/033659 A2 | 4/2005 |
| WO | WO 2005/065415 A2 | 7/2005 |
| WO | WO 2005/121759 A2 | 12/2005 |
| WO | WO 2007/060004 A1 | 5/2007 |
| WO | WO 2007/084367 A2 | 7/2007 |

* cited by examiner

LANCET WHEEL

CROSS REFERENCE TO RELATED APPLICATION

This application claims the benefit of European Patent Application No. 07 020 148.8 filed Oct. 15, 2007, which is hereby incorporated by reference in its entirety.

BACKGROUND

The invention is based on a lancet wheel that has the features specified in the preamble of claim 1. A lancet wheel of this type is known from WO 2007/060004 A1.

Lancet wheels of this type can be inserted into a puncturing device as lancet reservoir. The lancets of the lancet wheel are used consecutively in order to generate a puncturing wound in a body of a patient and to obtain a body fluid sample. For the highest possible convenience of use, it is important to ensure that the more or less tedious act of inserting a fresh lancet reservoir into the puncturing device needs to be performed as rarely as possible. This is especially true in the case of diabetics who need to check their blood sugar level several times daily and need to obtain a body fluid sample for this purpose. A lancet reservoir provided in the form of a lancet wheel is advantageous as compared to drum cartridges not only because of its relatively cost-efficient manufacturing, but also because a larger number of lancets can be arranged in a space-saving manner.

In lancet wheels of the type mentioned above, the tips of the lancets are erected prior to a puncture, for example by swiveling them out of the plane of the wheel. In this context, high precision is required in order for the lancet puncture to be associated with little pain. Moreover, erecting the lancet tips should be feasible with as little effort as possible to allow this to be performed in a compact puncturing device.

It is known from WO 2007/060004 A1 to debare kinking regions in a lancet wheel by means of embossing. If the lancet tip of a lancet wheel of this type is swiveled out of the plane of the wheel, the material in the region weakened by embossing yields such that a debared kink is generated. In the known lancet wheel, a force is exerted on the lancet in the region of the lancet tip in order to swivel the lancet tip and for the kinking. However, any contact of a part of the device with the tip of the lancet bears an inherent risk of contamination. Another disadvantage is that a lancet puncture is often experienced as painful by users of the known lancet wheel.

SUMMARY

It is the object of the invention to devise a way to improve the lancet wheel known from WO 2007/060004 A1.

This object is met by a lancet wheel that has the features specified in claim 1. Advantageous developments of the invention are the subject matter of the sub-claims. The object is also met by a puncturing system comprising a lancet wheel of this type.

A lancet wheel according to the invention has a carrier that carries the lancets, whereby the lancets are connected to the carrier by means of bars that allow for mobility of the lancets relative to the carrier. In this context, the bars of a lancet wheel according to the invention can have different functions.

A first possible function of the bars of a lancet wheel according to the invention is to facilitate the erecting of the lancet, i.e. facilitate a swivel motion relative to the carrier. For this purpose, it is sufficient to have a single bar each extend between a lancet and a neighboring part of the carrier. For erecting a lancet, a bar of this type can be bent using significantly less force as compared to an embossing running transversely through the lancet body, like the embossing that is present in the lancets of the lancet wheel known from WO 2007/060004 A1. In particular, the lancet does not need to be touched in the region of its tip for erecting it such that the risk of adversely impacting the lancet tip can be prevented.

A second possible function of the bars of a lancet wheel according to the invention is to provide for axial mobility of the lancet relative to the carrier and thus facilitate a lancet puncture that is associated with less pain. If a lancet is connected to the carrier on both sides by means of mutually concatenated bars, a puncturing motion can be performed with greater precision without a lateral shift that might lead to unnecessary pain.

In known lancet wheels, an erected lancet performs a motion that proceeds along a section of the arc of a circle, similar to the daisy wheel of a typewriter, during a puncture. During a puncture, this can lead to a lateral motion, i.e. a lateral shift, in the body of a patient that causes pain and enlarges the puncturing wound unnecessarily. Using mutually concatenated bars of a lancet wheel according to the invention allows for the implementation of a straight puncturing motion, i.e. it counteracts a lateral motion of this type.

Preferably, only two to three bars each are mutually concatenated. This is advantageous in that the axial mobility is achieved with minimal manufacturing effort. The mutually concatenated bars each preferably have one end of a bar connected to one end of a neighboring bar. Preferably arranged with their longitudinal sides next to each other, each of the concatenated bars positions itself slightly oblique to the plane of the lancet wheel during a puncture such that a zigzag-shaped configuration of the mutually concatenated bars results. This permits for mobility of the lancet in the direction of puncturing, i.e. perpendicular to the plane of the lancet wheel.

Preferably, the carrier is a frame that surrounds the lancets of the lancet wheel. It is particularly preferred in this context that the lancets of the lancet wheel each are surrounded by the frame on all sides. In this context, one or more lancets can be arranged in a window of the frame. Having a frame that surrounds the lancets is advantageous in that it increases the stability of the lancet wheel.

The lancet body preferably originates from a base, whereby the bars connect the lancet to the carrier via the base. Preferably, the base has a different width than the lancet body. If the bars, originating from the base, extend next to the lancet body, it is preferable for the base to be broader than the lancet body. However, the base can be connected to the carrier, for example, via a single bar just as well, whereby the bar extends in the longitudinal direction of the lancet body. In a case of this type, the base can be narrower than the lancet body just as well.

The lancets of a lancet wheel according to the invention are preferably aligned in radial direction. This allows an advantageous space-saving arrangement to be effected. However, it is feasible just as well to arrange the lancets in a different orientation.

A lancet wheel according to the invention can be manufactured from a circular metal disc, from which lancets, bars, and, fully or partly, the carrier are formed by cutting or etching. Aside from punching, in particular laser cutting is suitable for this purpose.

BRIEF DESCRIPTION OF THE DRAWINGS

Further details and advantages of the invention are illustrated in the following based on exemplary embodiments by making reference to the appended drawings. In this context, identical and corresponding parts are identified by identical reference numbers. The features of the invention described within the scope of the exemplary embodiments can be made to become the subject matter of claims either alone or in combination. In the figures:

FIG. 2b shows a side view relating to FIG. 2a;

DESCRIPTION OF THE SELECTED EMBODIMENTS

Figure 1:
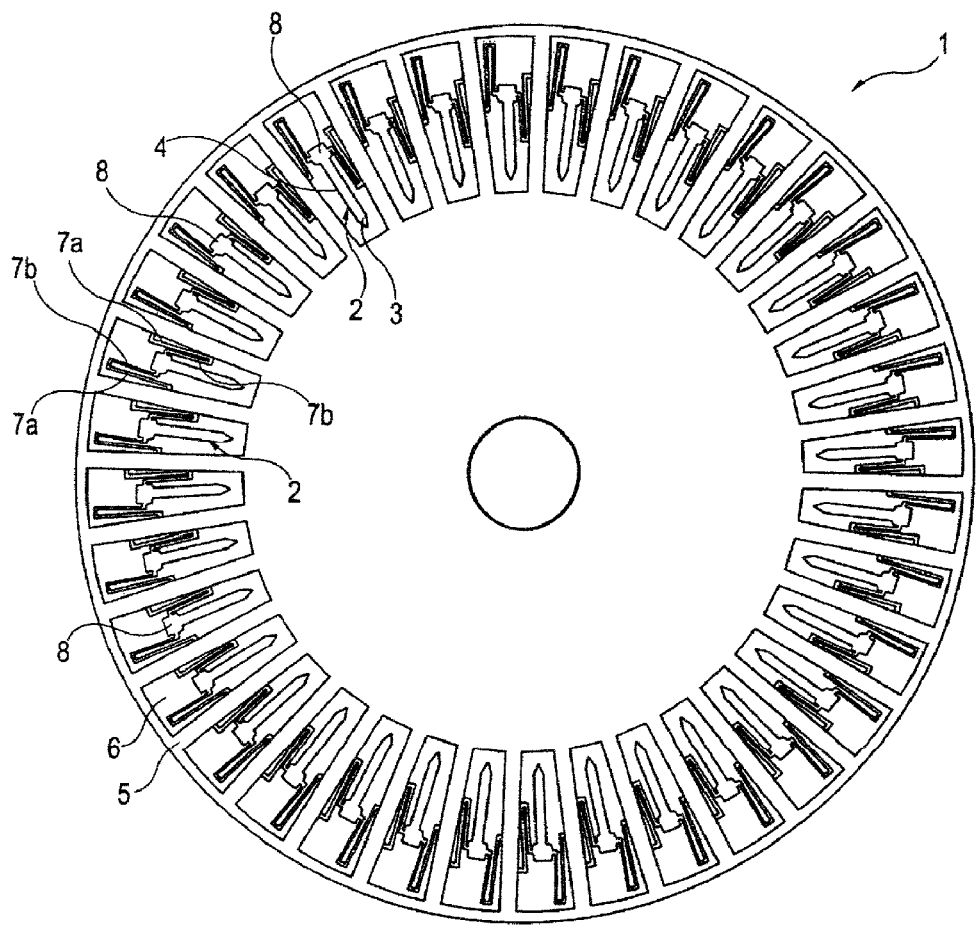
FIG. 1 shows an exemplary embodiment of a lancet wheel.

FIG. 1 shows an exemplary embodiment of a lancet wheel 1 that has a plurality of lancets 2 in a ring-shaped arrangement that comprise a lancet body 4 that ends in a lancet tip 3 and starts from a base 8. The lancet wheel 1 has a carrier 5 that is provided as frame and carries the lancets 2. In the exemplary embodiment shown, the frame 5 is a circular disc that comprises recesses 6 as windows, in which the lancets 2 are arranged. The lancets 2 are connected to the frame 5 via bars 7a, 7b that allow for mobility of the lancets 2 relative to the frame 5.

In the exemplary embodiment shown in FIG. 1, the lancets 2 each are connected to the frame 5 via two mutually concatenated bars 7a, 7b. The bars 7a, 7b are narrower than the lancet body 4 and each extends in the longitudinal direction of the lancet 2 that is connected to the frame 5 by them via its base 8. One of the concatenated bars 7a originates from the frame 5, another bar 7b originates from the lancet 2. The two concatenated bars 7a, 7b are arranged with their longitudinal sides being next to each other and are connected to each other by one of their ends each.

Figure 2A:
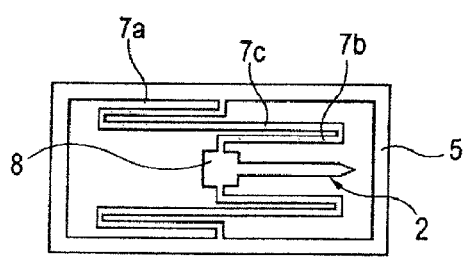
FIG. 2a shows a schematic view of an exemplary embodiment of a lancet and of the bars connecting the lancet to the frame of a lancet wheel.

FIG. 2a shows a further exemplary embodiment for developing the lancets 2 and the bars 7 connecting them to the frame 5. In the exemplary embodiment shown in a top view in FIG. 2a, the lancet 2 is connected to the lancet frame 5 on both sides via three mutually concatenated bars 7a, 7b, 7c each. Only part of the lancet frame 5 is shown in FIG. 2a. The frame extends ring-shaped and carries a plurality of lancets 2 in a ring-shaped arrangement similar to the exemplary embodiment shown in FIG. 1.

Figure 2B:

Like the lancet wheel shown in FIG. 1, the lancet wheel, of which part is shown in FIG. 2a, has been cut from a sheet metal disc and thus has the side view shown in FIG. 2b. Prior to a puncture, one lancet 2 is erected such that the side view shown in FIG. 3b and, for example, the top view shown in FIG. 3a result.

Figure 3A:
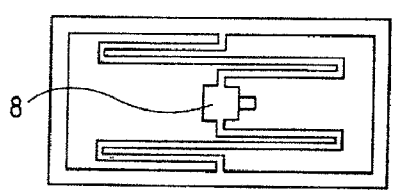
FIG. 3a shows the exemplary embodiment shown in FIG. 2a with the lancet erected.

In the exemplary embodiment shown in FIG. 3a, the lancet body 4 is bent away at its end facing the base 8, and the lancet 2 becomes erected thereby. In order to facilitate this bending away of the lancet body 4, the lancet body 4 can comprise an embossing by means of which the kinking site is defined. It is also feasible to twist the base 8 with respect to the frame 5 in order to erect the lancet 2.

Figure 3B:
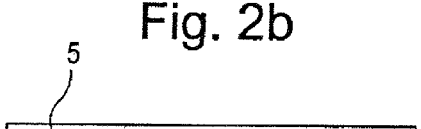
FIG. 3b shows a side view relating to FIG. 3a prior to a puncture.
Figure 4:
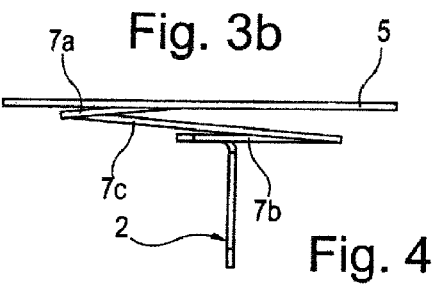
FIG. 4 shows a side view according to FIG. 3b during a puncture.

While the side view shown in FIG. 3b shows the situation existing prior to a puncture, FIG. 4 shows the lancet 2 and the bars 7a, 7b, 7c that concatenate it to the frame 5 during a puncture. It is shown in FIG. 4 that the mutually concatenated bars 7a, 7b, 7c lean over in oblique direction with respect to the plane of the frame 5 during a puncture. Since the mutually concatenated bars 7a, 7b, 7c are connected at their ends, this results in a zigzag-shaped configuration that allows the lancet 2 to move in the direction of puncturing.

The major advantage of the axial mobility of the lancets 2 that is effected by the mutually concatenated bars 7a, 7b, 7c is that the lancet 2 can perform a linear motion during a puncture. Lateral motions of a lancet 2 during a puncture would lead to pain. Since lateral motions, which would result, in particular, from a puncturing motion along a section of the arc of a circle, can be prevented by means of concatenated bars 7a, 7b, 7c, the exemplary embodiments described above allow a body fluid sample to be obtained with little pain.

To perform a puncture, a lancet 2 can be moved in the direction of puncturing, for example, by a plunger of a puncturing device that is not shown here, in which the lancet wheel 1 is inserted. A plunger of this type can engage the base 8 of a lancet 2 that is preferred to be wider than the body 4 of the lancet 2 originating from it.

Figure 5:
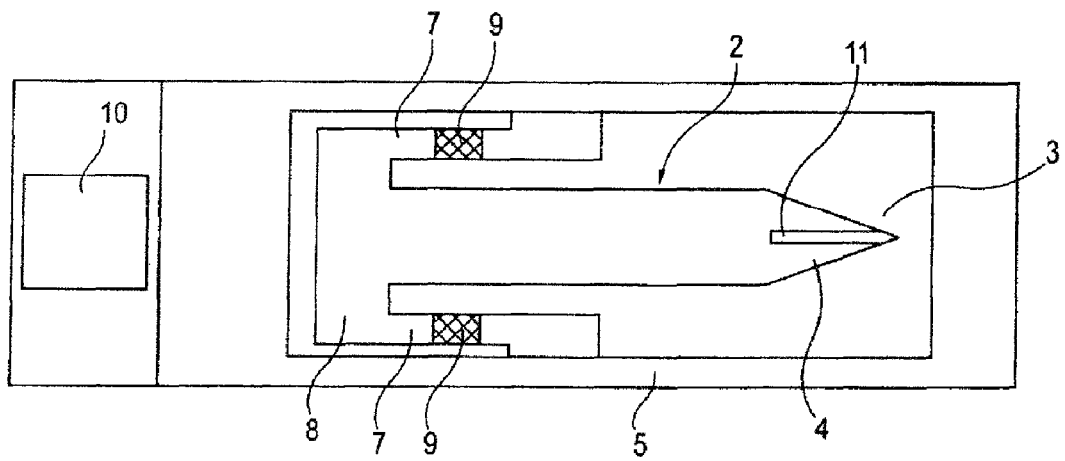
FIG. 5 shows a further exemplary embodiment of a lancet and of the bars connecting it to the frame of a lancet wheel.

FIG. 5 shows a further exemplary embodiment of a lancet 2 that is connected to a lancet frame 5 via bars 7. Similar to FIG. 2a, only a part of a lancet wheel is shown, in which the part shown in FIG. 5 repeats in a ring-shaped manner similar to the lancet wheel 1 shown in FIG. 1.

The exemplary embodiment shown in FIG. 5 differs from the exemplary embodiments described in the foregoing in that each lancet 2 is connected to the frame 5 on both sides by a single bar 7 only. When the lancet 2 becomes erected, the bars 2 bend at kinking sites 9. Since the bars 7 are narrower than the lancet body 4 of the lancet 2, preferably are less than half of their width, only little force is required for this purpose. In order to ease the process of bending even further, the bars 7 can have kinking sites 9 that are pre-conditioned by embossing or other type of structural weakening.

One advantage of the exemplary embodiment shown in FIG. 5 is that the lancet 2 can be erected by exerting pressure on the base 8. This is easily feasible using a suitable pin or stamp. The front area of the lancet body 4 facing the lancet tip 3 is not touched in the process such that there is no risk of contamination or other adverse influence on the lancet tip 3.

In the exemplary embodiment shown in FIG. 5, the lancet 2 contains at its tip 3 a sample reception facility 11 that can be provided, for example, as a capillary gap or bore hole. During a puncture, the sample reception facility 11 becomes filled with a body fluid sample. For analysis of the body fluid sample, the frame 5 carries a test field 10. The test field 10 preferably comprises detection reagents that permit a photometric or electrochemical assay of an analyte concentration to be performed. Test fields of this type are present in commercially available test strips, for example for blood sugar assay, and therefore need not be explained further.

The use of the lancet shown in FIG. 5 proceeds in the following steps. Firstly, the lancet 2 is erected, i.e. swiveled by a quarter arc of a circle with respect to the frame 5 in the exemplary embodiment shown. While the lancet is being erected, the bars 7 become bent at the kinking sites 9. Subsequently, the lancet 2 performs a rapid puncturing and returning motion during which the sample reception facility 11 takes up a body fluid sample. For analysis of the body fluid sample thus taken up, the lancet 2 is then swiveled again by a quarter arc of a circle with respect to the frame 5 such that the sample reception facility 11 comes to rest on the test field 10 that is installed on the frame 5. In order to ease the transfer of the body fluid sample to the test field 10, the latter preferably has an absorbent surface, for example a fleece.

The test field 10 can be arranged on the frame 5. However, the test field 10 is preferably arranged in a recess of the frame 5. This measure is advantageous in that any change of color of the test field 10 can be analyzed photometrically on the side of the frame 5 that is opposite to the lancet 2.

The exemplary embodiments described by means of FIGS. 1 to 4 can also be provided with a test field 10 and the corresponding lancets 2 can also be provided with a sample reception facility 11.

Figure 6:
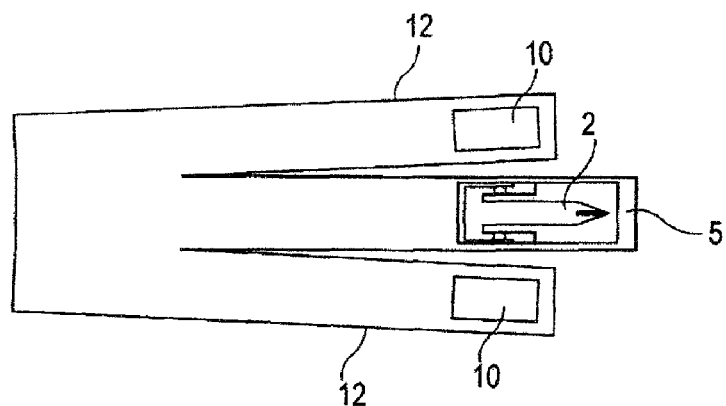
FIG. 6 shows a section of a further exemplary embodiment of a lancet wheel.

In order to dispense with the effort involved in having a sample reception facility 11, it is feasible just as well to arrange test fields 10 on the lancet wheel 1 on spring arms 12, each between the individual lancets 2. FIG. 6 shows a part of an exemplary embodiment of a lancet wheel, in which spring arms 12 carrying test fields 10 on their free ends are arranged between each of the lancets 2. In the exemplary embodiment shown in FIG. 6, sample reception proceeds in that the lancet wheel 1 is rotated further after a puncture such that a test field 10 comes to rest over the puncturing wound produced previously. Subsequently, the test field 10 is pressed against the puncturing wound such that a sample is taken up.

The exemplary embodiments of lancet wheels 1 and a matching puncturing device form a puncturing system. A puncturing device of this type has a swivel facility for erecting the lancets 2 of a lancet wheel 1 for a puncture, and a puncturing drive for moving an erected lancet for a puncture.

Figure 7:
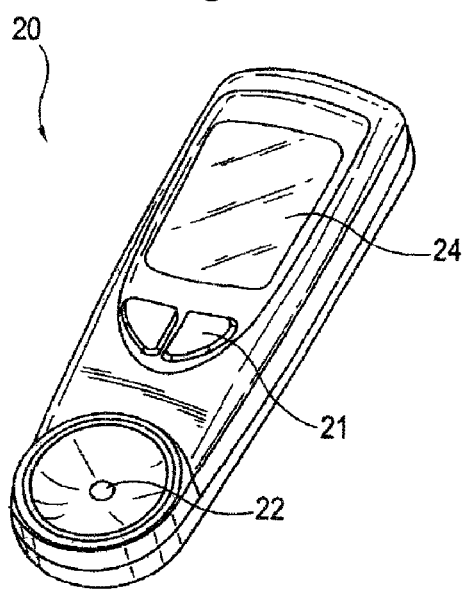
FIG. 7 shows an exemplary embodiment of a puncturing system.

FIG. 7 shows an exemplary embodiment of a puncturing device 20 of this type. The puncturing device 20 has a housing with a housing opening 22 to which a body part, in which a puncturing wound is being generated, is touched, operating elements 23 in the form of keys, and a display facility 24 in the form of a liquid crystal display for display of analytical results. The puncturing device 20 has a reception compartment (not shown) for a lancet wheel 1. The reception compartment has a lockable opening that is situated on the back of the exemplary embodiment shown in FIG. 7.

In addition to the swivel facility mentioned above and the puncturing drive, a transport facility is also arranged in the puncturing device 20 and can be used to rotate a lancet wheel 1 that is inserted in the puncturing device 20 such that its lancets 2 can be moved consecutively into a use position, in which they can be used to generate a puncturing wound in a body part that is touched against the device opening 22.

In order to exclude contamination of the lancets 2 of a lancet wheel 1 while inserting said lancet wheel 1 into a puncturing device 20, the lancet wheels 1 described by means of FIGS. 1 to 6 can be covered on both sides by a sterile protective film. The sterile protective film gets broken when the lancet 2 is being erected such that it does not interfere with a puncturing motion. The sterile protective films can be provided with openings for the test fields 10 in order not to adversely influence the reception of a sample. It is feasible just as well to use ring-shaped sterile protective films that cover the lancet tips that are to be protected while leaving the test fields without cover.

After a puncture, a spent lancet 2 can be broken off from the lancet wheel 1 and disposed by a user. However, preferably the lancet wheel 1 with a spent, but still erected lancet 2 is rotated further and the lancet 2 is bent back to its original position by renewed motion of the lancet wheel 1 in the direction of puncturing. For this purpose, an oblique surface can be arranged on the interior of the housing 23 against which a spent, erected lancet 2 impinges and thus is bent back.

REFERENCE NUMBERS

1 Lancet wheel
2 Lancets
3 Lancet tip
4 Lancet body
5 Frame
6 Recesses
7 Bars
7a Bars
7b Bars
7c Bars
8 Base
9 Kinking sites
10 Test field
11 Sample reception facility
12 Spring arms
20 Puncturing device
21 Operating elements
22 Housing opening
23 Housing
24 Display facility

The invention claimed is:

1. Lancet wheel, comprising:
a plurality of lancets in a ring-shaped arrangement, said lancets including a lancet body that ends in a lancet tip;
a carrier that carries the lancets, wherein the carrier extends within a plane, wherein the lancets are connected to the carrier via bars that permit mobility of the lancets relative to the carrier out of the plane of the carrier;
wherein the lancets lie flat within the plane of the carrier; and
wherein the bars are bendable to allow the lancets bend out of the plane of the carrier during lancing.

2. Lancet wheel according to claim 1, wherein the carrier is a frame that surrounds the lancets.

3. Lancet wheel according to claim 1, wherein the bars each extend in the longitudinal direction of the lancet they connect to the carrier.

4. Lancet wheel according to claim 1, wherein the bars extend, at least in part, along the lancet they connect to the carrier.

5. Lancet wheel according to claim 1, wherein the lancets are connected on both sides to the carrier via mutually concatenated bars.

6. Lancet wheel according to claim 5, wherein the mutually concatenated bars connecting a lancet to the carrier are arranged longitudinally next to each other.

7. Lancet wheel according to claim 5, wherein at least one of the concatenated bars extends along the lancet body beyond an end of the lancet body facing away from the lancet tip.

8. Lancet wheel according to claim 1, wherein the lancet body originates from a base, whereby the bars connect the lancets to the carrier via the base.

9. Lancet wheel according to claim 1, further comprising test fields for analysis of a body fluid sample.

10. Lancet wheel according to claim 9, wherein the test fields are carried by spring arms that are arranged between the lancets.

11. Lancet wheel, comprising:
a plurality of lancets in a ring-shaped arrangement, said lancets including a lancet body that ends in a lancet tip;

a carrier that carries the lancets, wherein the carrier extends within a plane, wherein the lancets are connected to the carrier via bars that permit mobility of the lancets relative to the carrier out of the plane of the carrier, wherein each of the bars has a kinking site where the bars are configured to be bent when the lancet is erecting; and wherein each lancet is connected on both sides to the carrier via at least one of the bars.

12. Lancet wheel according to claim 11, wherein each of the bars are configured with a structural weakening at the kinking site to facilitate bending of the bars for erecting the lancets out of the plane of the carrier during puncturing.

13. Lancet wheel according to claim 12, wherein each of the bars have an embossment at the kinking site.

14. Lancet wheel, comprising:
a plurality of lancets in a ring-shaped arrangement, said lancets including a lancet body that ends in a lancet tip;
a carrier that carries the lancets, wherein the carrier extends within a plane, wherein the lancets are connected to the carrier via bars that permit mobility of the lancets relative to the carrier out of the plane of the carrier; and
wherein the bars are narrower than the lancet body.

15. Puncturing system, comprising:
a lancet wheel that comprises a plurality of lancets in a ring-shaped arrangement, said lancets comprising a lancet body that ends in a lancet tip, and a frame that carries the lancets, wherein the frame extends within a plane, wherein the lancets are connected to the frame via bars that allow for mobility of the lancets relative to the plane of the frame,
wherein the lancets extend within the plane of the frame at a first position,
a swivel facility for erecting the lancets of the lancet wheel for a puncture, wherein the swivel is configured to bend the bars of the lancet to a second position where the lancet is erected orthogonal to the plane of the frame, and
a puncturing drive for moving an erected lancet for a puncture.

16. The puncturing system of claim 15, further comprising:
each of the lancets including a sample reception facility in which body fluid is received; and
each of the lancets having an associated test field received on the frame, the test field being located to receive the body fluid from the sample reception facility upon further bending of the lancets after creating the puncture.

17. A lancet wheel, comprising:
a carrier having a ring shape, wherein the carrier extends within a plane;
a plurality of lancets oriented in a ring-shaped arrangement within the carrier, wherein each of the lancets has a base and a lancet tip that extends from the base;
both sides of each lancet are configured to be connected to the carrier via at least a first bar and a second bar, wherein the first bar has one end connected to the carrier, wherein the second bar has one end connected to the base of the lancet, wherein the first bar and the second bar extend in a longitudinal direction relative to the lancet tip; and
wherein the first bar and the second bar are coupled to one another to form a zigzag configuration during lancing to permit movement of the lancet in a direction perpendicular to the plane of the carrier while minimizing lateral movement of the lancet.

18. The lancet wheel of claim 17, further comprising a third bar joined between the first bar and the second bar.

* * * * *